| United States Patent [19]
Bender et al.

[11] 3,996,364
[45] Dec. 7, 1976

[54] 9-XANTHYLAMINOALKYLPYRIDINE DERIVATIVES

[75] Inventors: Paul E. Bender, Willingboro, N.J.; Bernard Loev, Broomall; Carl David Perchonock, Philadelphia, both of Pa.

[73] Assignee: SmithKline Corporation, Philadelphia, Pa.

[22] Filed: Aug. 6, 1975

[21] Appl. No.: 602,157

[52] U.S. Cl. .......................... 424/263; 260/296 T
[51] Int. Cl.$^2$ ...................................... C07D 405/12
[58] Field of Search ................. 260/296 T; 424/263

[56] References Cited
UNITED STATES PATENTS 3,647,816   3/1972   Draber et al. ...................... 260/309

OTHER PUBLICATIONS

Villani, et al., J. Med. Chem., vol. 18, No. 1, pp. 1–8 (1–75).
Neth. Appl. 6,511,532 (3–11, 66) cited as C.A. 65:3847–3848 (1966).

*Primary Examiner*—Henry R. Jiles
*Assistant Examiner*—C. Jaisle
*Attorney, Agent, or Firm*—Joseph A. Marlino; Richard D. Foggio; William H. Edgerton

[57]   ABSTRACT

9-Xanthylaminoalkylpyridine derivatives are prepared. These compounds are inhibitors of gastric acid secretion.

8 Claims, No Drawings

9-XANTHYLAMINOALKYLPYRIDINE DERIVATIVES

This invention relates to new 9-xanthylaminoalkylpyridines having pharmacological activity. These compounds inhibit gastric acid secretion.

The compounds of this invention are represented by the following formula:

FORMULA 1

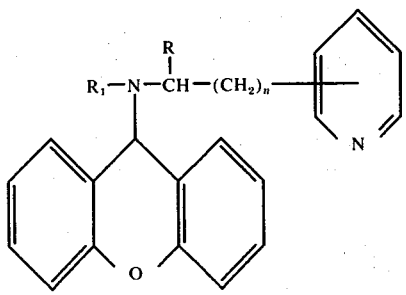

in which:
R is hydrogen or lower alkyl of from 1 to 3 carbon atoms straight or branched chain;
$R_1$ is hydrogen or lower alkyl of from 1 to 3 carbon atoms straight or branched chain; and
$n$ is from 0 to 3;
or a pharmaceutically acceptable acid addition salt thereof.

Preferred compounds of this invention are represented by Formula 1 above when R and $R_1$ are hydrogen or methyl.

An advantageous compound of this invention is 9-[β-(2'-pyridyl)-isopropylamino]xanthene.

The compounds of this invention may be used in the form of a pharmaceutically acceptable acid addition salt having the utility of the free base. The pharmaceutically acceptable acid addition salts of the compounds of Formula 1 are formed with organic and inorganic acids by methods known to the art. The base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of such organic salts are those with maleic, fumaric, benzoic, ascorbic, pamoic, succinic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids as well as with the 8-halotheophyllines, for example, 8-bromotheophylline. Exemplary of such inorganic salts are those with hydrochloric, hydrobromic, sulfuric, sulfamic, phosphoric, and nitric acids. These salts may also be prepared by the classical method of double decomposition of appropriate salts which is well known to the art.

Further some compounds of this invention contain at least one asymmetric carbon atom and are resolvable into d- and l- optical isomers. Unless otherwise specified in the description and accompanying claims, it is intended to include all isomers whether separated or mixtures thereof.

The compounds of this invention produce inhibition of gastric acid secretion. This activity is demonstrated by administration to pylorus ligated rats at doses of about 1.0 to 50 mg./kg. orally and at about 1.25 to 20 mg./kg. intraduodenally. Also, this activity is demonstrated by administration to chronic gastric fistula rats at doses of about 30 mg./kg. orally and to chronic fistula monkeys at doses of about 1.9 to 15 mg./kg. by intragastric administration. In these procedures, compounds which produce an increase in gastric pH or a decrease in gastric juice volume titratable acidity or acid output are considered active.

At a dose of 10 mg./kg. orally, an advantageous compound of this invention, 9-[β-(2'-pyridyl)isopropylamino]xanthene, decreased the acid output by 73% in pylorus ligated rats and by 90% intraduodenally. The same compound decreased the acid output by 80% when given to monkeys at a dose of 7.5 mg./kg. orally.

These compounds which inhibit gastric acid secretion are useful in treating gastric and duodenal ulcer disease and other conditions involving gastric acid hypersecretion.

The compounds of this invention are prepared by the following procedures:

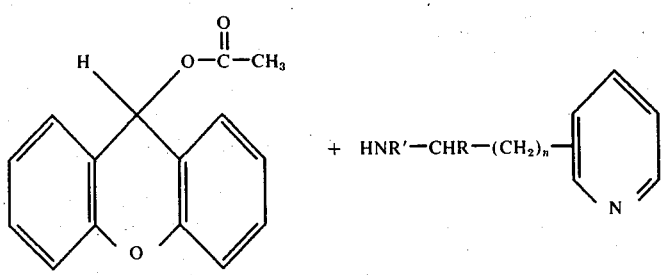

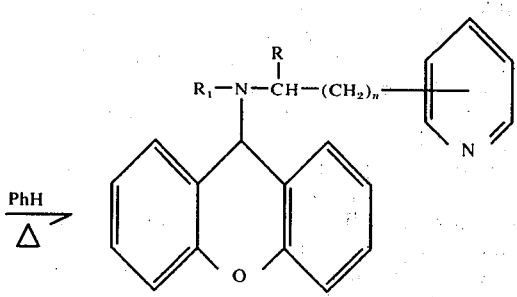

in which R, $R_1$ and $n$ are as defined in Formula 1. Thus, as shown above, a 9-xanthenyl alkanoate is reacted with an aminopyridine. The reaction is preferably carried out in an inert solvent such as benzene or toluene at elevated temperature, conveniently at reflux temperature.

The 9-xanthenyl alkanoate starting materials are either known to the art or are prepared from xanthydrols by reacting with a lower isocyanate to give a 9-lower alkylcarbamoyloxyxanthene and reacting that intermediate with a lower alkanoic acid.

The xanthydrols are either known to the art or are prepared by the following procedure. A 2-halobenzoic acid is reacted with a phenol preferably in the presence of a base such as potassium carbonate and in the presence of cuprous iodide and copper bronze. The resulting 2-phenoxybenzoic acid is cyclized by treating with acid for example polyphosphoric acid. The resulting xanthone is reduced, for example using sodium amalgam in ethanol, to give the xanthydrol.

The aminopyridine starting materials are also either known to the art or are prepared by known procedures.

Preferably, the compounds are administered in conventional dosage forms prepared by combining an appropriate dose of the compound with standard pharmaceutical carriers.

Pharmaceutical compositions having gastric acid secretion inhibitory activity, in dosage unit form, comprising a pharmaceutical carrier and a gastric acid secretion inhibiting amount of a compound of Formula 1 or a pharmaceutically acceptable acid addition salt thereof are objects of this invention.

The pharmaceutical carrier may be for example a solid or a liquid. Exemplary of solid carriers are lactose, magnesium stearate, terra alba, sucrose, talc, stearic acid, gelatin, agar, pectin, acacia or cocoa butter. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example the preparation may take the form of tablets, capsules, powders, suppositories, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The methods of inhibiting gastric acid secretion in accordance with this invention comprise administering internally to an animal an effective amount of a compound of Formula 1 or a pharmaceutically acceptable acid addition salt thereof. The active ingredients will preferably be administered in dosage unit form as described above.

The compounds of this invention will be administered in a daily dosage regimen of from about 10 mg. to about 2 g., preferably from about 25 mg. to about 1 g. Advantageously, equal doses will be administered one to four times per day. Dosage units will contain from about 10 mg. to about 500 mg., preferably from about 25 mg. to about 300 mg., of the active ingredient.

When administration is carried out as described above, gastric acid secretion is inhibited.

One skilled in the art will recognize that in determining the amounts of the active ingredients in the claimed compositions and used in the claimed methods, the activity of the chemical ingredient as well as the size of the host animal must be considered.

The foregoing is a general description of how to prepare the compounds of this invention. The following examples illustrate the preparation of specific compounds having gastric acid secretion inhibiting activity. However, this should not be construed as a limitation of the invention since appropriate variations in the starting materials will produce other products set forth hereinabove.

EXAMPLE 1

Methyl isocynate (20 g.) is added slowly, with stirring, to a filtered solution of 30 g. of xanthydrol in 100 ml. of anhydrous triethylamine. After standing for 40 minutes in a 20° C. water bath, the mixture is filtered. The collected solid is washed with anhydrous diethyl ether and dried in vacuo to give 9-(N-methylcarbamoyloxy)xanthene.

To 15 g. of 9-(N-methylcarbamoyloxy)xanthene, suspended in 200 ml. of dry ether, is added 18 ml. of glacial acetic acid with stirring. After 1 hour, the lower acid layer is removed. The ether phase is then cooled, neutralized with cold aqueous sodium bicarbonate, dried over anhydrous magnesium sulfate and concentrated in vacuo. The residue is recrystallized from benzene-hexane to give 9-acetoxyxanthene, m.p. 109°–112° C.

A solution of 4.0 g. of 9-acetoxyxanthene and 2.0 g. of 4-aminomethylpyridine in 100 ml. of benzene is refluxed for 24 hours. The reaction mixture is stripped of solvent and the residue dissolved in ether. The ether solution is washed with cold 5% sodium carbonate and water and dried over potassium carbonate and chromatographed with alumina and eluting with ether/hexane. The eluate is extracted with ether/acetone and concentrated in vacuo to give 4-pyridylmethyl-9-xanthylamine having a m.p. of 83°–85° C.

EXAMPLE 2

A solution of 4.9 g. of 9-acetoxyxanthene and 2.78 g. of β-(2-pyridyl)isopropylamine in benzene is refluxed for 19 hours. The solution is washed with aqueous sodium bicarbonate, dried and evaporated in vacuo. The residue is chromatographed over silica gel eluting with ether followed by acetone. Concentration of the eluate yields 9-[β-(2'-pyridyl)isopropylamino]xanthene.

EXAMPLE 3

By the procedure of Example 2, using the following aminopyridines in place of β-(2-pyridyl)isopropylamine:
- 2-(3-aminopropyl)pyridine
- 2-(2-methylaminoethyl)pyridine
- 2-(4-aminopentyl)pyridine
- 2-(2-ethylaminoethyl)pyridine
- 3-(methylaminoethyl)pyridine
- 2-(2-aminoethyl)pyridine
- 3-aminomethylpyridine
- 2-aminomethylpyridine the following products are respectively obtained:
- 9-[3-(2-pyridyl)propylamino]xanthene
- 9-[N-methyl-N-(β-2-pyridylethyl)amino]xanthene
- 4-(9'-xanthydrylamino)-1-(2''-pyridyl)pentane
- 9-[N-ethyl-N-(β-2-pyridylethyl)amino]xanthene
- 9-[N-methyl-N-(3-pyridylethyl)amino]xanthene
- 2-(2-xanthen-9-ylaminoethyl)pyridine
- 3-xanthen-9-ylaminomethylpyridine
- 2-xanthen-9-ylaminomethylpyridine

EXAMPLE 4

| Ingredients | Amounts |
| --- | --- |
| N-(4-Pyridylmethyl)-9-xanthenylamine | 200 mg. |
| Lactose | 75 mg. |
| Magnesium stearate | 5 mg. |

The ingredients are mixed and filled into a hard gelatin capsule. One capsule is administered 3 times a day.

EXAMPLE 5

| Ingredients | Amounts |
| --- | --- |
| 9-[β-(2'-pyridyl)-isopropylamino]xanthene | 150 mg. |
| Peanut oil | 100 mg. |

The ingredients are mixed and filled into a soft gelatin capsule. Two capsules are administered 4 times a day.

What is claimed is:

1. A chemical compound of the formula:

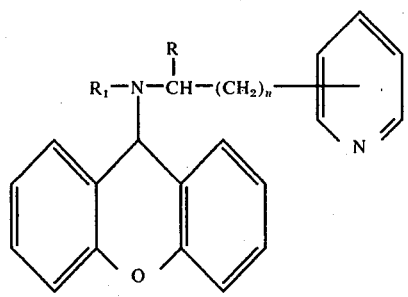

or a pharmaceutically acceptable acid addition salt of said compound in which:

R is hydrogen or lower alkyl of from 1 to 3 carbon atoms;

$R_1$ is hydrogen or lower alkyl of from 1 to 3 carbon atoms;

$n$ is from 0 to 3.

2. A chemical compound according to claim 1 in which R is lower alkyl.

3. A chemical compound according to claim 2 in which R is methyl.

4. A chemical compound according to claim 3 in which $R_1$ is hydrogen.

5. A chemical compound according to claim 1 said compound being 9-[β-(2'-pyridyl)isopropylamino]xanthene.

6. A chemical compound according to claim 1 in which $R_1$ is lower alkyl and R is hydrogen.

7. A pharmaceutical composition in dosage unit form having gastric acid secretion inhibitory activity comprising a pharmaceutical carrier and a chemical compound as defined in claim 1.

8. A method of inhibiting gastric acid secretion which comprises administering internally to animals a chemical compound as defined in claim 1 in an amount sufficient to produce said inhibition.

* * * * *